(12) United States Patent
Iwakiri et al.

(10) Patent No.: US 9,084,435 B2
(45) Date of Patent: Jul. 21, 2015

(54) YEAST MUTANT AND YEAST EXTRACT

(75) Inventors: Ryo Iwakiri, Oita (JP); Hirokazu Maekawa, Saiki (JP); Naohisa Masuo, Saiki (JP); Shogo Furue, Saiki (JP); Hiroko Kodera, Saiki (JP); Setsuko Hirakura, Saiki (JP); Masahiro Nishida, Saiki (JP); Masanori Uchida, Saiki (JP); Sakiko Ikeda, Saitama (JP)

(73) Assignee: KOHJIN CO., LTD., Tokyo (JP)

( * ) Notice: Subject to any disclaimer, the term of this patent is extended or adjusted under 35 U.S.C. 154(b) by 589 days.

(21) Appl. No.: 12/810,624

(22) PCT Filed: Mar. 26, 2009

(86) PCT No.: PCT/JP2009/056168
§ 371 (c)(1), (2), (4) Date: Aug. 4, 2010

(87) PCT Pub. No.: WO2009/123019
PCT Pub. Date: Oct. 8, 2009

(65) Prior Publication Data
US 2011/0020528 A1    Jan. 27, 2011

(30) Foreign Application Priority Data

Mar. 31, 2008 (JP) ................................ 2008-091709
Apr. 22, 2008 (JP) ................................ 2008-111232

(51) Int. Cl.
| | |
|---|---|
| C12N 1/16 | (2006.01) |
| A23L 1/30 | (2006.01) |
| A23L 1/221 | (2006.01) |
| C12P 13/14 | (2006.01) |
| C12P 19/32 | (2006.01) |
| C12R 1/72 | (2006.01) |

(52) U.S. Cl.
CPC .............. *A23L 1/3016* (2013.01); *A23L 1/221* (2013.01); *A23L 1/3018* (2013.01); *C12P 13/14* (2013.01); *C12P 19/32* (2013.01); *C12R 1/72* (2013.01)

(58) Field of Classification Search
None
See application file for complete search history.

(56) References Cited

U.S. PATENT DOCUMENTS 3,914,450 A * 10/1975 Robbins et al. ............... 426/533

FOREIGN PATENT DOCUMENTS

| | | | |
|---|---|---|---|
| EP | 0805202 | * | 5/1997 |
| JP | B2-07-093871 | | 10/1995 |
| JP | A-09-294581 | | 11/1997 |
| JP | A-09-313169 | | 12/1997 |
| JP | A-10-327802 | | 12/1998 |
| JP | A-2001-103458 | | 4/2001 |
| JP | A-2002-171961 | | 6/2002 |
| JP | A-2006-129835 | | 5/2006 |
| WO | WO 99/16860 A1 | | 4/1999 |

OTHER PUBLICATIONS

"Monthly Food Research," No. 627, pp. 72-75, 2007.
Messenguy et al., "Regulation of Compartmentation of Amino Acid Pools in *Saccharomyces cerevisiae* and Its Effects on Metabolic Control," *Eur. J. Biochem.*, vol. 108, pp. 439-447, 1980.
International Search Report issued in Application No. PCT/JP2009/056168; Mailed on Apr. 21, 2009 (With Translation).

* cited by examiner

*Primary Examiner* — Irene Marx
(74) *Attorney, Agent, or Firm* — Oliff PLC

(57) ABSTRACT

The present invention provides a natural yeast extract having a high-impact first taste by containing glutamic acid in a large amount. Further, the present invention provides a yeast extract having strong umami by containing 5'-guanylic acid or 5'-inosinic acid in a large amount. In addition, the present invention provides a yeast mutant accumulating glutamic acid, glutamine, and ribonucleic acid in a large amount for obtaining the yeast extract.

A yeast mutant inducing a natural mutation to which organic acid-tolerance or organic acid analogue-tolerance is imparted accumulates free glutamic acid and glutamine in such a significant amount as a total amount of 10% by weight or more in a cell, and further accumulates ribonucleic acid in an amount of 5% by weight or more. A yeast extract produced using the above yeast mutant contains L-glutamic acid in an amount of 20% by weight or more, and further contains 5'-IG in an amount of 3% by weight or more.

1 Claim, No Drawings

YEAST MUTANT AND YEAST EXTRACT

TECHNICAL FIELD

The present invention relates to: a yeast mutant accumulating free L-glutamic acid and L-glutamine, and ribonucleic acid in significant amounts in a cell; and a yeast extract obtained using the yeast containing natural L-glutamic acid in a high concentration and exhibiting good taste (umami) having a strong first taste.

BACKGROUND ART

Following in addition to the trend towards healthy products, natural products, and additive-free products, problems on the safety of foods, such as bovine spongiform encephalopathy (BSE), expectations for a yeast extract that is a natural seasoning have been rapidly increased. As a yeast extract, a nucleic acid-based extract in which a rich taste or an aftertaste is strengthened, and a peptide-based extract imparting a body or thickness of the taste to foods, which are recently attracting attentions, are actively developed.

On the other hand, as a method of adding a yeast extract in which umami having first taste is strengthened and which is represented by glutamic acid, a method of adding inexpensive purified sodium glutamate (MSG) from the outside is well known and examples for developing the yeast extract itself are not so many.

For example, as shown in Patent Document 1, there is a method of producing a yeast extract in which a glutamic acid content is enhanced by enlarging an amount of free glutamic acid accumulated in a yeast through mutation breeding, or as shown in Patent Document 2, there is also an attempt to enhance a glutamic acid content by keeping an extract extraction rate low and further by improving the production method such as treating with an enzyme.

However, the glutamic acid content in thus produced yeast extract is 14.5% or less converted into the content of a sodium salt thereof. Since the value is lower than that of a wheat gluten hydrolysate that is typically used as a glutamic acid-containing seasoning, it is not at a thoroughly satisfying level as for tastes.

Further, there are such problems as the lowering of the cell yield per sugar by a mutation breeding in Patent Document 1, and the limitation of the production method due to a low amount of glutamic acid accumulated in a yeast in Patent Document 2.

For developing a yeast extract having a high glutamic acid content by various production methods corresponding to a production design with productivity capable of meeting the industrial application, it is necessary to spectacularly enlarge the amount of glutamic acid accumulated in a yeast without lowering the productivity of the cell.

While sodium glutamate produced by using bacteria is accumulated outside of a cell, in the production of a yeast extract, glutamic acid is necessary to be accumulated within a yeast cell. However, it is conjectured that in the cell, a metabolism control system such as a feedback inhibition acts, so that it is not easy to accumulate glutamic acid in a high concentration within the cell.

There is such a report that by an analysis of the pool of free amino acids in a yeast cell, it is found that glutamic acid is present in large quantity in a cytoplasm and glutamine is present in large quantity in a vacuole (Eur. J. Biochem. Vol. 108, p. 439 (1980)). Thus, if a yeast accumulating in a high concentration, not only glutamic acid, but also glutamine that is differentially-localized can be developed, by an enzymatic conversion of glutamine, which is a usual method, the production of a yeast extract in which the glutamic acid content is extremely enhanced, is possible.

In Patent Document 3, by a gene recombination of *Saccharomyces cerevisiae* which is a monoploid laboratory yeast, a recombinant strain accumulating free glutamic acid and glutamine in a total amount of 5.4% is built and from this yeast, a yeast extract having a glutamic acid content of 16.2% is produced. However, even by using a gene recombination, yet the total amount of glutamic acid and glutamine is low and it is not more than that the glutamic acid content of the obtained yeast extract is a little over 20% converted into the content of a sodium salt thereof. In addition, the similar gene recombination by industrial yeasts with high ploidy and with a lowered sporulation ability or by *Candida utilis* yeast having no sporulation ability is difficult. Further, it is not a desirable method at present to apply the produced gene recombinant to foods, because there are barriers such as the control of a law and a resistance of consumers.

Thus, there is such a necessity that for producing a yeast extract containing glutamic acid in a high concentration, the gene recombination is not used, and a yeast accumulating free glutamic acid and glutamine in a high concentration in a cell by a natural mutation is bred.

Further, a synergistic effect of glutamic acid and 5'-guanylic acid or 5'-inosinic acid for the taste is well known and for producing a yeast extract having strong umami, it is preferred to use a strain containing besides the above amino acids, ribonucleic acid (RNA), which is a raw material for nucleotide, also in a high concentration.

Patent Document 1: Japanese Patent Application Publication No. JP-A-9-294581
Patent Document 2: Japanese Patent Application Publication No. JP-A-2006-129835
Patent Document 3: Japanese Patent Application Publication No. JP-A-2002-171961

DISCLOSURE OF THE INVENTION

Problem to be Solved by the Invention

In view of the above, the present invention provides a natural yeast extract having a high-impact first taste by containing glutamic acid in a large amount. In addition, the present invention provides a yeast extract having strong umami by containing 5'-guanylic acid or 5'-inosinic acid in a large amount. Further, the present invention provides a yeast mutant accumulating glutamic acid, glutamine and ribonucleic acid in a large amount for obtaining such a yeast extract.

The present inventors have made extensive and intensive studies toward eliminating the above drawbacks. As a result, the inventors find that a yeast to which organic acid-tolerance or organic acid analogue-tolerance is imparted by inducing mutation surprisingly accumulates free glutamic acid and glutamine in such a significant total amount as 10% by weight or more in the cell and further accumulates ribonucleic acid in an amount of 5% by weight or more, and completed the present invention.

In other words, the present invention provides the following aspects:

(1) a yeast mutant, in which free glutamic acid and glutamine are accumulated in a total amount of 10% or more, based on a weight of a dry cell;

(2) the yeast mutant according to (1), in which ribonucleic acid (RNA) is further accumulated in an amount of 5% or more, based on a weight of a dry cell;

(3) the yeast mutant according to (1) or (2), in which the yeast mutant is tolerant to ethyl bromopyruvate;

(4) the yeast mutant according to (1) or (2), in which the yeast mutant is tolerant to ethyl bromopyruvate and 2-oxoglutaric acid;

(5) the yeast mutant according to any one of (1) to (4), in which the yeast mutant is *Candida utilis* 36D61 (accession number: FERM BP-11103);

(6) a yeast extract produced from the yeast mutant as described in any one of (1) to (5), in which the yeast extract contains L-glutamic acid in an amount of 20% by weight or more converted into an amount of a sodium salt thereof; and (7) the yeast extract according to (6), in which the yeast extract further contains 5'-guanylic acid and 5'-inosinic acid or 5'-adenylic acid in a total amount of 3% by weight or more.

Effects of the Invention

Although the yeast mutant according to an embodiment of the present invention is a strain obtained without performing a gene recombination, it accumulates glutamine and glutamic acid in significant amounts, further accumulates also ribonucleic acid in a large amount. A yeast extract obtained using this strain exhibits umami having a strong first taste due to a high glutamic acid content and further exhibits a strong umami due to a synergistic effect of inosinic acid and guanylic acid.

By adding such a yeast extract to foods, satisfying umami can be imparted to foods with a small amount of the yeast extract and without adding glutamic acid from the outside, and particularly umami property having a strong first taste can be imparted.

Here, "first taste" according to an embodiment of the present invention means a taste spreading swiftly in the mouth at the moment a food is contained in the mouth, a taste corresponding mainly to amino acids, not to a sugar or a common salt, which is based on the sensitive time of monosodium glutamate (MSG). In addition, "continuity" means the length of time in which a taste felt after the first taste is retained.

BEST MODES FOR CARRYING OUT THE INVENTION

As the yeast used according to an embodiment of the present invention, an edible yeast is preferred and examples thereof include a yeast belonging to *Saccharomyces*, a yeast belonging to *Kluyveromyces*, a yeast belonging to *Candida* and a yeast belonging to *Pichias*. Preferably recommended is a yeast belonging to *Candida*, that is, *Candida utilis* known to have high ribonucleic acid-accumulating function. It is also possible to apply another yeast that has improved according to a procedure shown in Japanese Examined Patent Application Publication No. JP-B-07-93871 to enlarge the amount of accumulated ribonucleic acid.

Although the present invention has characteristic in terms of using a yeast accumulating free glutamic acid, glutamine and ribonucleic acid in a high concentration for producing a yeast extract containing glutamic acid exhibiting a strong first taste in a high concentration, such a yeast can be obtained by using a mutagenizing agent such as ultraviolet rays, X-rays, nitrous acid, nitrosoguanidine and ethylmethane sulfonate and by selecting a strain capable of growing on a synthetic medium containing organic acids or organic acid analogues in a concentration with which the parent strain thereof cannot grow. As the organic acid analogue used, those related to the biosynthesis of glutamic acid are preferred. Specific examples of the organic acid analogue include ethyl bromopyruvate (hereinafter, abbreviated to BPE) and 2-oxoglutaric acid (hereinafter, abbreviated to 2OG). With respect to the former, although bromopyruvic acid known as a pyruvic acid analogue is used for causing a yeast to accumulate glutamic acid in a high concentration in Japanese Patent Application Publication No. JP-A-9-313169, for breeding a *Candida* yeast, an ethyl compound thereof, that is, ethyl bromopyruvate is effective. The latter is known as an inhibitor of citric acid synthase and as shown in Japanese Patent Application Publication No. JP-A-2001-103958, 2OG is used in improving a yeast accumulating malic acid or succinic acid in the outside of a cell for improving the flavor of sake. However, a yeast *Candida utilis* has tolerance to such a high concentration as more than 2,000 ppm of this agent, so that it is difficult to obtain a tolerance strain by using an individual agent. By using both agents in combination, it is possible to breed a yeast accumulating free glutamic acid and glutamine in a high concentration more effectively than using the agent individually. Further, by repeating a mutation treatment to impart tolerance to both agents in a high concentration, a yeast accumulating free glutamic acid and glutamine in a total amount of 10% by weight or more can be obtained.

Thus isolated *Candida utilis* 36D61 strain is extremely preferred for the production of a yeast extract accumulating free glutamic acid and glutamine in a total amount of 14% by weight and ribonucleic acid in an amount of 9% by weight, containing glutamic acid in a high concentration and having a strong first taste, or for the production of a yeast extract containing glutamine.

For example, as shown in Japanese Patent Application Publication No. JP-A-9-294581, there is such a fear that the productivity of the cell may be lowered by a mutation breeding, however, the yeast mutant used in the embodiment of the present invention maintains a high cell yield per sugar and there is no problem with respect to the industrial production thereof.

A culture form according to an embodiment of the present invention may be any of a batch-wise culture and a continuous culture, however, the latter is adopted in terms of industrial productivity.

For a medium for culturing the mutant according to an embodiment of the present invention, as a carbon source, glucose, acetic acid, ethanol, glycerol, molasses, sulfite waste liquid, etc. are used and as a nitrogen source, urea, ammonia, ammonium sulfate, ammonium chloride, nitrate salts, etc. are used. As a source for phosphoric acid, potassium and magnesium, a usual industrial raw material such as calcium superphosphate, ammonium phosphate, potassium chloride, potassium hydroxide, magnesium sulfate and magnesium chloride may be used. Besides them, to the medium, inorganic salts of zinc, copper, manganese, iron, or the like are added. As others, vitamins, amino acids, nucleic acid-related substances, etc. are not specially used however, needless to say, these substances or organic substances such as corn steep liquor, casein, yeast extract, meat extract and peptone may be added.

A culture temperature is preferably 21 to 37° C., more preferably 25 to 34° C. and pH for the culture is preferably 3.0 to 8.0, more preferably 3.5 to 7.0. Since the productivity of amino acids or nucleic acids varies depending on the culture condition, it is necessary to adopt conditions suitable for the production specification of an objective yeast extract.

By using the above obtained yeast accumulating free glutamic acid and glutamine in a high concentration, the production of a yeast extract containing glutamic acid in an amount of 20 to 50% converted into the amount of a sodium salt thereof can be easily performed according to a production method known for the production of the yeast extract.

The extraction can be performed by any of methods typically used in the production of a yeast extract, for example, a heating-extraction method, an enzymolysis method and an autolysis method. Each of the taste of the obtained yeast extracts has characteristics and an extraction method corresponding to a production design can be selected. Hereinafter, a hot water extraction and an enzyme extraction having extraction rates largely different from each other are exemplified as follows, however the extraction method is not limited thereto.

In a production method by the hot water extraction, a cell suspension prepared in a concentration of 10% is heated at 50° C. or more, preferably 60° C. or more. The extraction time varies depending on the extraction condition and is around several seconds to several hours. Glutamine has low thermal stability and thus, is preferably subjected to small heat history. In the hot water extraction, a yeast extract having a low peptide content and thus, having a clear taste can be produced.

On the other hand, for the enzyme extraction, an enzyme typically used in the digestion of a yeast, a cell wall digesting enzyme and protease are applicable. A yeast extract produced by an enzyme extraction contains more extracted components than that produced by a hot water extraction. Therefore, since the former yeast extract has a higher peptide ratio, a body is imparted to the taste.

After the extraction, solid contents are removed by a method such as a centrifugation to obtain an extracted component.

For further enhancing a glutamic acid concentration in the yeast extract, as frequently used for foods, a commercially available glutaminase is made to act on the yeast extract during extracting the extract or after the isolation of the extracted component to convert glutamine to glutamic acid.

This yeast can accumulate, besides the above compounds, RNA in an amount of 9% by weight or more. For example, by a method described in Japanese Examined Patent Application Publication No. JP-B-7-93871, RNA is extracted from the yeast and ribonuclease is made to act, and depending on the case deaminase is further made to act. Thus, a yeast extract containing 5'-adenylic acid and 5'-guanylic acid (hereinafter, expressed as 5'-AG) or 5'-inosinic acid and 5'-guanylic acid (hereinafter, expressed as 5'-IG) can also be produced at a time. For the extraction of RNA, the heat inactivation of an enzyme by heating is effective, however, since glutamine has poor thermal stability, it is advantageous, for example, to set an optimal temperature or time for the extraction or to heat and reextract the cell after a hot water extraction.

When 5'-phosphodiesterase is made to act for decomposing RNA in the extracted liquid to 5'-nucleotide or when deaminase is made to act, if desired for converting 5'-adenylic acid in a liquid containing thus obtained 5'-nucleotide to 5'-inosinic acid, it may react under recommended conditions using a commercially available enzyme. Specific examples of the reaction conditions include conditions disclosed in Japanese Examined Patent Application Publication No. JP-B-7-93871.

5'-nucleotide exhibits a synergistic action of glutamic acid and the taste and is effective for strengthening umami of first taste.

After the completion of the reaction, for inactivating the enzyme utilized, the reaction solution is heated at 90 to 100° C. for around 30 to 60 minutes and thereafter, the solid content is removed by a method such as a centrifugation. Next, a supernatant is concentrated to paste or is processed to powder by further drying. A concentration method and a drying method are not particularly limited, however, a drying method, by which the reaction solution is not subjected to an excessively high temperature, such as a vacuum concentration method, a freeze-drying method and a spray drying method, is used.

EXAMPLES

Hereinafter, the present invention is described in detail referring to examples.

Here, an analysis method and an evaluation method are as follows. (Quantification method of glutamic acid and glutamine in yeast cell)

The quantification of free glutamic acid and glutamine in a yeast cell was performed as follows.

A washed cell was heated in boiling water for 4 minutes, was cooled in running water, and then was centrifuged. The resultant supernatant liquid was appropriately diluted to quantify glutamic acid and glutamine by using a bio-sensor (trade name: BF-5; manufactured by Oji Scientific Instruments) equipped with each enzyme electrodes for glutamic acid and for glutamine.

(Quantification Method of RNA in Yeast Cell)

The quantification of RNA in the yeast cell was performed according to Schmidt-Tanhaeuser-Schneider method (J. Biol. Chem. Vol. 164, p. 747 (1946)).

The dry weight of the cell was measured by a method including: taking a sample of 10 mL of a washed yeast suspension into a weighing bottle; volatilizing a water content from the suspension by heating at 105° C. for 20 hours; leaving the resultant residue to be cooled to room temperature in a desiccator; and measuring the difference in the weight of the residue between before and after the heating using a precision electronic balance. Based on this dry weight of the yeast cell, the content (in % by weight) of each component in the cell was calculated.

(Quantification Method of Free Glutamic Acid and Other Free Amino Acids in Powder Yeast Extract)

The concentrations of free glutamic acid and free other amino acids, and the total amino acid concentration in the dry powder yeast extract were measured according to a common procedure using an amino acid analyzer (trade name: L8800; manufactured by Hitachi, Ltd.).

(Quantification Method of 5'-Nucleotide in Powder Yeast Extract)

5'-nucleotide in the dry powder yeast extract was quantified under conditions disclosed in Japanese Examined Patent Application Publication No. JP-B-7-93871 using a high performance liquid chromatography.

(Sensory Evaluation)

The sensory evaluation of the extract was performed as follows.

A sample was prepared by dissolving in warm water, 1% of a powder extract and a common salt so that the concentration of the common salt during drinking the sample becomes 0.3%. By panelists capable of recognizing umami of MSG in a concentration of 0.05 g/dL, the difference between "strength of first taste", "continuity" and "strength of umami" and those of the control plot were evaluated in seven criteria and the result of the evaluation was expressed in the average value. Here, the criteria of the evaluation of first taste, continuity and umami in seven criteria evaluation are as follows. "+3 points: extremely strong, +2 points: considerably strong, +1 point: somewhat strong, 0 point: there was no difference with "control plot", −1 point: somewhat weak, −2 points: considerably weak, −3 points: extremely weak".

Example 1

Obtaining Mutant

The strain of *Candida utilis* ATCC 9950 was cultured in a test tube containing a YPD medium (yeast extract 1%, polypeptone 2%, glucose 2%) till the logarithmic growth phase. This cell was recovered and washed and thereafter, the cell was subjected to a mutagenizing treatment according to a method of Adelberg et, al. using nitrosoguanidine (Biochem. Biophys. Res. Comm. Vol. 18, p. 788 (1965)). The cell subjected to a mutagenizing treatment was washed twice and then was cultured on a YPD medium at 30° C. over one night to prepare a mutagenizing-treated cell.

The cell was cultured on a selected medium prepared by adding to a synthetic medium (containing 2% by weight of glucose, 2% by weight of monopotassium phosphate, 0.1% by weight of ammonium sulfate, 0.05% by weight of magnesium sulfate, 0.2% by weight of urea, 8.6 ppm of ferric sulfate, 14.6 ppm of zinc sulfate, 0.7 ppm of copper sulfate, 3.3 ppm of manganese sulfate and 2% by weight of agar), 40 to 45 ppm of ethyl bromopyruvate (BPE) or further 100 to 200 ppm of 2-oxoglutaric acid (2OG) at 30° C. for 3 to 7 days. As a result, colonies growing on a selected medium on which the parent strain thereof cannot grow were isolated. These colonies were cultured on the above synthetic liquid medium and strains exhibiting advantageous cell-productivity and accumulating free glutamic acid and glutamine in a large amount were selected. Specifically, first, BPE0128 strains having BPE 40 ppm-tolerance were obtained and next, by repeating the above operations relative to these strains, 2OG3D4 strains having double tolerance of BPE 40 ppm and 2OG 100 ppm were obtained, and by further repeating mutagenizing treatment in the same manner, 36D61 strains which are the yeast mutant according to an embodiment of the present invention and which have double tolerance of BPE 45 ppm and 2OG 200 ppm were obtained.

Next, the parent strain and the obtained mutant were cultured in a 30 L fermenter-scale to confirm the productivity. A test strain was yeast cultured beforehand in a conical flask containing a YPD medium and was 0.5 to 1.5%-inoculated in the 30 L fermenter. At this time, the medium composition was "glucose: 6% by weight, monopotassium phosphate: 2% by weight, ammonium sulfate: 1.4% by weight, magnesium sulfate: 0.06% by weight, ferric sulfate: 10 ppm, zinc sulfate: 18 ppm, copper sulfate: 1 ppm, manganese sulfate: 8 ppm". The culture was performed under conditions "liquid amount in the fermenter: 15 L, pH (automatically controlled with ammonia): 4.3, temperature for culture: 30° C., aeration: 1 vvm, stirring: 400 rpm". The obtained cells were analyzed and the result is shown in Table 1.

(Table 1)

TABLE 1

Productivity of culturing mutant

| Strain | Marker (ppm) | Glu (%) | Gln (%) | Glu + Gln (%) | Cell yield per sugar (%) |
| --- | --- | --- | --- | --- | --- |
| ATCC9950 | — (parent strain) | 2.13 | 0.95 | 3.08 | 51.19 |
| BPE0128 | BPE40 | 2.63 | 1.46 | 4.09 | 50.37 |
| 2OG3D4 | BPE40 + 2OG-100 | 3.32 | 1.44 | 4.76 | 50.70 |
| 36D61 | BPE45 + 2OG-200 | 4.30 | 10.08 | 14.38 | 52.66 |

TABLE 1-continued

Productivity of culturing mutant

| Strain | Marker (ppm) | Glu (%) | Gln (%) | Glu + Gln (%) | Cell yield per sugar (%) |
| --- | --- | --- | --- | --- | --- |

When the total amount of free glutamic acid and glutamine accumulated of the mutant is compared with the amount of the parent strain, while in an ethyl bromopyruvate-tolerant strain (BPE0128), the total amount was enlarged by 30%, in high concentration ethyl bromopyruvate and 2-oxoglutaric acid-tolerant strain (36D61), the total amount was enlarged surprisingly to about 4 times. At this time, the RNA content of 36D61 strain was 9.7%.

The yeast *Candida utilis* 36D61 strain has the identical mycological characteristics, except drug tolerance, to those of the parent strain ATCC 9950. In addition, this strain exhibited vital growth also on a medium containing glycerol and ethanol as carbon sources.

*Candida utilis* 36D61 strain was deposited in National Institute of Advanced Industrial Science and Technology; International Patent Organism Depositary as accession number: PERM BP-11103 on Mar. 18, 2008.

Example 2

Obtaining Yeast Extract

For the experimental production of the yeast extract, a continuous culture liquid of *Candida utilis* mutant 36D61 strain was used. A test strain was yeast cultured beforehand in a conical flask containing a YPD medium and was 0.5 to 1.5%-inoculated in a 5 L-volume fermenter. The medium composition was the same as that in the above 30 L batchwise culture. The culture was performed under conditions "liquid amount in the fermenter: 2 L, pH: 4.3 (automatically controlled with ammonia), temperature for culture: 30° C., aeration: 1 vvm, stirring: 600 rpm". At this time, the specific growth rate was 0.24 to 0.25 harsh −1. The obtained cell was analyzed and the results were as follows. Total amount of free glutamic acid and glutamine: 13.9% by weight (glutamic acid: 4.7% by weight, glutamine: 9.2% by weight), cell yield per sugar: 56.8%.

The continuous culture liquid was recovered while cooling it with ice and yeast cells were collected by centrifugation to obtain wet yeast cell. The obtained cell was re-suspended in water and was centrifuged to obtain about 160 g as a dry weight of cell. The obtained yeast cell was suspended in water and the total volume thereof was messed up to 1.6 L. Next, the suspension of the yeast cell was heated in a hot water bath and after the temperature reached 70° C., an extract was extracted while maintaining the temperature at 70° C. and stirring the suspension for 10 minutes. Immediately thereafter, the suspension was cooled in running water and insoluble solid contents were removed by centrifugation to obtain an extract. The temperature of the obtained extract was lowered to 50° C. and then, a solution in which 4.4 g of glutaminase (trade name: Daiwa C100S; manufactured by Daiwa Fine Chemicals Co., Ltd.) were dissolved in a small amount of water was added to the extract, followed by reacting the resultant mixture at 40 to 60° C. for 5 hours while stirring the mixture. The resultant extract was heated at 90 to 95° C. for 30 minutes and was cooled, and thereafter, insoluble solid contents in the extract were removed again by centrifugation. Next, the resultant extract was concentrated using a rotary evaporator and the resultant concentrate was freeze-dried to obtain about 49 g of a powder yeast extract. The extract extraction rate at this time was about 25% and the free glutamic acid content in the extract was 54.5% by weight converted into the content of a sodium salt thereof. In addition, at this time, the free amino acid content was 64.2% by weight and the total amino acid content was 72.3% by weight. From these contents and the following equation, the peptide content was calculated, and was found to be 8.1% by weight.

Peptide content(%)=total amino acid content(%)−free amino acid content(%)

The obtained yeast extract aqueous solution has considerably strong MSG-like umami and first taste, which are high-impact tastes never present in a conventional yeast extract. In addition, the yeast extract has a little yeast odor, a moderate thickness of taste and a clear aftertaste, so that the yeast extract has preferred tastes.

In the experimental production, a sensory evaluation of the extracts before and after the glutaminase reaction was performed. A part of the extracts before and after the glutaminase reaction was collected as a sample and was dissolved in warm water so that the concentration of the dissolved solid content becomes 1%. In the resultant solution, a common salt was also dissolved so that the concentration of the common salt during drinking the sample becomes 0.3%. "Strength of first taste", "continuity" and "strength of umami" of the extract after the glutaminase reaction were evaluated by 5 panelists relative to those of the extract before the glutaminase reaction as the control plot. Here, the glutamic acid concentration measured with BF-5 was 20% before the glutaminase reaction and 51% after the glutaminase reaction as converted into the content of a sodium salt thereof.

As a result, the sample after the glutaminase reaction had first taste, continuity and umami of respectively +2.6, +1.8 and +2.2 and it could be confirmed that the umami and the first taste were markedly enhanced. In addition, the sample after the reaction had a totally strong taste and a thickness of taste was also felt.

Example 3

In substantially the same manner as in Example 2, a cell of *Candida utilis* mutant 36D61 strain having a dry weight of about 21 g was obtained. The obtained cell was analyzed and as a result, the total amount of glutamic acid and glutamine was found to be 14.3% by weight (glutamic acid: 5.0% by weight, glutamine: 9.3% by weight) and the cell yield per sugar was found to be 56.1%.

Water was added to the above obtained yeast and the total volume was messed up to 200 mL. Next, the resultant suspension was heated in a warm water bath and after the temperature reached 90° C., the suspension was heated at 90° C. for 2 minutes. Immediately thereafter, the suspension was cooled in running water to lower the temperature of the suspension to 50° C. and thereafter, a solution in which 0.2 g of a cell wall digesting enzyme (trade name: Tunicae; manufactured by Amano Enzyme Inc.) were dissolved in a small amount of water was added thereto, followed by reacting the resultant mixture at 50° C. for 1 hour while stirring the mixture. Insoluble solid contents were removed from the reaction mixture after the completion of the reaction by centrifugation to obtain an extract. To the obtained extract, 0.56 g of glutaminase C100S were added and the reaction, concentration and drying were performed in substantially the same manner as in Example 2 to obtain about 11 g of a powder yeast extract. The extract extraction rate was about 51% and the free glutamic acid content in the extract was 31.9% by weight converted into the content of a sodium salt thereof. In addition, at this time, the free amino acid content was 39.0% by weight; the total amino acid content was 53.1% by weight; and the peptide content was 14.1% by weight. Although this solution had a little poor strength, it had the same tastes as those in Example 2.

Example 4

In substantially the same manner as in Example 2, a cell of *Candida utilis* mutant 36D61 strain having a dry weight of about 20 g was obtained. The obtained cell was analyzed and as a result, the total amount of glutamic acid and glutamine, and the amount of RNA were found to be respectively 12.5% by weight (glutamic acid: 4.7% by weight, glutamine: 7.8% by weight), and 9.0% by weight, and the cell yield per sugar was found to be 56.2%.

Water was added to the above obtained yeast and the total volume was messed up to 200 mL. Next, the resultant suspension was heated in a warm water bath and the suspension was heated at 90° C. for 5 minutes. Immediately thereafter, the suspension was cooled in running water to lower the temperature of the suspension to 50° C. and thereafter, a solution in which 0.2 g of a cell wall digesting enzyme (trade name: Tunicae; manufactured by Amano Enzyme Inc.) were dissolved in a small amount of water was added thereto, followed by reacting the resultant mixture at 50° C. for 6 hour while stirring the mixture. Insoluble solid contents were removed from the reaction mixture after the completion of the reaction by centrifugation to obtain an extract. To the obtained extract, 0.47 g of glutaminase C100S was added and in a similar manner as in Example 2, after the completion of the reaction, the reaction mixture was warmed to 65° C. To the reaction mixture, a solution in which 30 mg of 5'-phosphodiesterase (trade name: ribonuclease P; manufactured by Amano Enzyme Inc.) was dissolved in a small amount of water was added and the reaction was effected at the same temperature for 3 hours while stirring the reaction mixture. Next, the temperature of the reaction mixture was lowered to 45° C. and to the reaction mixture, a solution in which 20 mg of deaminase (trade name: deamizyme; manufactured by Amano Enzyme Inc.) were dissolved in a small amount of water was added. The reaction mixture was maintained at this temperature for 2 hours while stirring the reaction mixture. Thereafter, the reaction mixture was heated at 90 to 95° C. for 30 minutes and was left to be cooled. Subsequently, insoluble solid contents were removed by centrifugation and the reaction mixture was concentrated and dried to obtain about 12 g of a powder yeast extract. The extract extraction rate was about 60% and the free glutamic acid content in the extract was 23.2% by weight converted into the content of a sodium salt thereof. The 5'-IG content was 3.3% by weight. In addition, at this time, the free amino acid content was 32.1% by weight, the total amino acid content was 44.8% by weight, and the peptide content was 12.7% by weight.

The obtained yeast extract aqueous solution had a little yeast odor, a high-impact taste, strong umami, and further continuity and a thickness of the taste, so that the yeast extract has extremely well balanced tastes.

Example 5

In substantially the same manner as in Example 2, a cell of *Candida utilis* mutant 36D61 strain having a dry weight of about 20 g was obtained. The obtained cell was analyzed and as a result, the total amount of glutamic acid and glutamine, and the amount of RNA were found to be respectively 12.1% by weight (glutamic acid: 4.8% by weight, glutamine: 7.3% by weight), and 8.8% by weight, and the cell yield per sugar was found to be 56.6%.

Water was added to the above obtained yeast and the total volume was messed up to 200 mL, followed by heating the resultant suspension in a warm water bath. Next, the suspension was subjected to a heating treatment in substantially the same manner as in Example 4 and was cooled in running water to 50° C. of the suspension temperature. Subsequently, a 6N sodium hydroxide was added to make pH of the suspension 10 and the suspension was stirred for 3 hours. Insoluble solid contents were removed from the reaction mixture after the completion of the reaction by centrifugation to obtain an extract. The obtained extract was subjected to glutaminase, 5'-phosphodiesterase and deaminase reactions in substantially the same manner as in Example 4. Thereafter, the reaction mixture was heated at 90 to 95° C. for 30 minutes and was left to be cooled. Subsequently, insoluble solid contents were removed by centrifugation and the reaction mixture was concentrated and dried to obtain about 10 g of a powder yeast extract. The extract extraction rate was about 43% and the free glutamic acid content in the extract was 28.1% by weight converted into the content of a sodium salt thereof. The 5'-IG content was 5.4% by weight. In addition, in this extract, the free amino acid content was 36.6% by weight, the total amino acid content was 42.6% by weight, and the peptide content was 6.0% by weight.

The obtained yeast extract aqueous solution had the same glutamic acid content as that in Example 3, however, by an effect of 5'-IG, a considerably strong first taste and umami were felt and further, the continuity of taste was also felt. The solution had smaller rough tastes than that in Example 4 and had clear flavor.

The yeast extract according to an embodiment of the present invention was subjected to a sensory evaluation.

A yeast extract was experimentally produced from 2OG3D4 strain in substantially the same manner as in Example 2, except that the glutaminase reaction was omitted. "Strength of umami", "strength of first taste" and "continuity" of the powder extract obtained by each production method were evaluated by 7 panelists relative to a powder yeast extract containing glutamic acid in an amount of 12.0% by weight converted into the amount of a sodium salt thereof as the control plot.
(Table 2)

TABLE 2

| Yeast extract | Content in powder extract (% by weight) | | | Evaluation | | |
|---|---|---|---|---|---|---|
| | Glu | 5'-IG | Peptide | Umami strength | First taste strength | Continuity |
| Control plot (2OG3D4) | 12.0 | <1% | 8.00 | 0 | 0 | 0 |
| Example 2 | 54.5 | <1% | 8.1 | 2.6 | 2.2 | 1.5 |
| Example 3 | 31.9 | <1% | 14.1 | 1.0 | 1.1 | 0.4 |
| Example 4 | 23.2 | 3.3 | 12.7 | 2.0 | 2.0 | 1.0 |
| Example 5 | 29.2 | 5.2 | 6.0 | 2.1 | 2.3 | 1.4 |

* The Glu and 5'-IG contents are expressed in a content calculated by converting into that as a sodium salt thereof.

As is apparent from Table 2, the yeast extract obtained from the yeast mutant obtained according to an embodiment of the present invention has a free glutamic acid content apparently higher than that of 2OG3D4 strain as the control plot irrespective of the extraction method used and has a higher 5l'-IG content. Then, it is also apparent that the yeast extract according to an embodiment of the present invention having such characteristics exhibits umami having a strong first taste.

INDUSTRIAL APPLICABILITY

According to some aspects of the present invention, a yeast extract having an extremely high glutamic acid content can be produced and a natural umami seasoning having a strong first taste can be provided. The seasoning is preferably used to foods requiring umami having a strong first taste.

In addition, the yeast mutant according to some aspects of the present invention accumulates glutamine in a significant amount. Glutamine is considered to be effective for the proliferation and the functional expression of an immunocyte and can be utilized as a yeast cell and a yeast extract as a supplement utilizing the function.

Accession Number
  Accession number: PERM BP-11103
  The invention claimed is:
  1. A yeast mutant of *Candida utilis*, wherein:
    the yeast mutant is *Candida utilis*36D61, accession number: FERM BP-11103;
    free glutamic acid and glutamine are accumulated in a total amount of 10% or more, based on a total dry cell weight;
    ribonucleic acid (RNA) is accumulated in an amount of 5% or more, based on the total dry cell weight; and
    the yeast mutant is tolerant to ethyl bromopyruvate and 2-oxoglutaric acid.

* * * * *